United States Patent [19]

Schuldt

[11] Patent Number: 5,025,653
[45] Date of Patent: Jun. 25, 1991

[54] GAS DETECTION SYSTEM

[75] Inventor: Hans P. Schuldt, Ditzingen, Fed. Rep. of Germany

[73] Assignee: Conducta Gesellschaft fur MeB- und Regeltechnik, Gerlingen, Fed. Rep. of Germany

[21] Appl. No.: 359,479

[22] Filed: May 31, 1989

[30] Foreign Application Priority Data

Jun. 4, 1988 [DE] Fed. Rep. of Germany ....... 3819128

[51] Int. Cl.$^5$ ............................................. G01N 27/00
[52] U.S. Cl. ....................................... 73/1 G; 73/23.2
[58] Field of Search ............... 73/1 G, 23, 27 R, 23.2; 340/632, 633, 634; 422/83, 98

[56] References Cited

U.S. PATENT DOCUMENTS

| | | | |
|---|---|---|---|
| 4,390,869 | 6/1983 | Christen et al. | 340/634 |
| 4,404,399 | 1/1985 | Youngman | 73/1 G |
| 4,464,653 | 8/1985 | Winner | 340/632 |
| 4,526,028 | 7/1985 | Hubner | 340/632 |
| 4,555,930 | 12/1985 | Leach et al. | 73/1 G |
| 4,704,607 | 11/1987 | Teather et al. | 73/1 G |
| 4,854,153 | 8/1989 | Miyagawa et al. | 73/1 G |

FOREIGN PATENT DOCUMENTS 2655271 6/1978 Fed. Rep. of Germany .
86/06528 11/1986 World Int. Prop. O. .......... 340/632

Primary Examiner—Robert Raevis
Attorney, Agent, or Firm—Darby & Darby

[57] ABSTRACT

In a gas detection system for detecting the content of inflammable, explosive and/or toxic or other gases an arrangement is proposed according to which a central electronic evaluation system is connected to a plurality of measuring heads, which are installed at the points of measurement, by a single common two-wire line and each measuring head is provided, at its place of installation, with its own intelligence (microprocessor) for processing at least partly the values supplied by the sensor, each measuring head being equipped with at least two sensors of different types or measuring ranges and with an additional temperature sensor and each sensor having an identification which is indicative of the type and measuring range of the sensor and which is picked up by the measuring head. The electronic evaluation system and the measuring heads communicate with each other by bidirectional digital communication, after the measuring heads have been addressed, and the measuring head is supplied with current via the two-wire line.

20 Claims, 3 Drawing Sheets

O　　TOX　　UEG　　IRA

GAS DETECTION SYSTEM

BACKGROUND OF THE INVENTION

The invention relates to a gas detection system.

Gas detection systems, where a plurality of sensors detecting the presence of gases and their respective quantities are connected to a common central evaluation system, have been known in many different, though complicated and complex, forms.

For example, a system suited for monitoring larger garages or tunnels is designed in such a manner that gas sampling heads are arranged at different points and connected to a common evaluation center via mechanical hose connections the length of which may reach several hundred meters and even more. The gas mixture is supplied from different sampling points to the sensor in the evaluation center for analysis by switching over cyclically from one hose to the next, which action is usually effected by means of solenoid valves. This system uses of course only one sensor. Apart from the enormous mechanical input required not only for the initial installation, but also for the subsequent monitoring operations, for example with a view to preventing bending or breaking of certain hoses, such a measuring method is also particularly lengthy because important dead times result from the fact that the hoses must be scavenged every time before the gas sensor can be supplied with new gas to be measured. Such a system requires a great number of mechanically moving parts, particularly high performance of its pumps, frequent servicing operations, and all these circumstances are connected with the disadvantage that no redundancy of measurements is obtained, that any self-monitoring of the system is excluded and that the cycle times may be in the range of 30 minutes and above.

One has therefore built up a gas detection system in such a manner that each of the points at which monitoring operations or measurements are to be effected is equipped with a measuring head provided with a sensor and that the measuring heads are connected to an electronic evaluation system via a 5-wire line, under certain circumstances only via a 3-wire line. In the case of a 5-wire line, two of the wires serve for firing the sensor, or for supplying it with current, two other wires serve for transmitting the measured value from the measuring head to the electronic evaluation system, and a fifth wire serves as connection to earth. In the case of a 3-wire line, the earth wire performs simultaneously the function of one line of each of the two other pairs of lines. If another gas analysis is required at the same point or, as usually intended in the case of such systems, at a different point, identical parallel systems, comprising a measuring head and a separate connection cable, must be guided to the electronic evaluation system for detecting the second gas component or gas mixtures at different points, which means that the cost of the system and its installation is quite considerable.

In addition, it is a problem of such known gas detection systems that it is not possible to combine different types of equipment because of the different supply voltages for the measuring heads, different sensitivities and connections. In addition, these systems require separate balancing of the electronic evaluation system up to the measuring head, after assembly and installation of each head, and lengthy calibration operations which will be described hereafter in more detail.

Certain measuring heads require high, other measuring heads require lower supply currents, depending among other things on the sensor and the gases to be monitored, i.e. whether inflammable, toxic, explosive or other gases are to be detected, and in addition the very low analog signal voltages are responsible for the extremely high sensitivity to disturbing voltages which is normally a characteristic of such systems. Consequently, it has been general practice to install the individual connection lines between the individual measuring heads and the electronic evaluation system, whether they are of the 5-wire or of the 3-wire type, in the form of shielded cables. Normally, each measuring head is provided with a separate power pack feeding the sensor connected to it. Because of the many different requirements, measuring ranges, types of gases to be analyzed, and the like, one has heretofore never succeeded at arriving at a standardization in the meaning of a desirable simplification.

It has been known in connection with certain chemical sensors, i.e. such with low current consumption, to supply the measuring head with a weak supply current and to feed back a measuring signal via the same line, in which case the supply current may, for example, be in the range of maximally 4 mA, while the measuring system may be in the range of between 4 ... 20 mA.

However, in the case of these known systems, the calibration of the sensors, which has to be effected particularly frequently, is also very troublesome and has in any case to be effected every time the sensor is exchanged, and in addition the sensor must always be connected to the one measuring head to which it is assigned.

The before-mentioned calibration may be carried out, for example, in such a manner that one service person is present at the central station, i.e. near the electronic evaluation system, while another service person, equipped with cylinders containing test gas of a given concentration, is present at the very place, i.e. the place of the respective sensor, to supply the latter with the desired test gas. The two persons at the central station and at the place of the sensor, respectively, communicate via walkie-talkie. Every time the respective sensor has been supplied with test gas in sufficient concentration, until an equilibrium has been achieved, this fact, and the type of test gas used, is then communicated to the service person waiting at the central station who then performs the calibration process on the setting potentiometers at the central station, provided no change of concentration has occurred in the meantime for some reason or other. This calibration method is lengthy and susceptible to trouble due to the fact that it has to be carried out by two people so that calibration errors are frequently encountered. Other problems encountered with the methods according to the prior art are connected with the fact that the shielded wires can be run only over a maximum length of 1500 m, due to the high current of the measuring head and the susceptibility to trouble of the weak signals of the measuring head. In addition to the high cost of installation, it is also necessary in this connection to balance the bridge current of the measuring head relative to the length of the line, and of course also relative to zero and the sensitivity.

Given the fact that the known gas detection systems do not comprise any "site electronics"—this term is being newly introduced by the present invention—one further requires, in addition to the balancing potentiometer for the bridge current in relation to the length of the line, one balancing potentiometer for zero point, one balancing potentiometer for sensitivity (measuring-head signals voltage), balancing potentiometers for the first and the second alarms, test jacks for bridge current and measuring-head signal (aging) and a separate possibility to balance the sensor or the head manually using an external measuring instrument, and all this without the possibility to combine different types of measuring components in the component carrier.

Now, it is the object of the present invention to remedy all these inconveniencies and to improve the known gas detection systems in such a manner that it is now possible, without great input of work and cost, to arrange measuring heads at any desired point, which measuring heads are capable of determining simultaneously, i.e. in parallel, the concentration of a plurality of gases and of communicating fully with the electronic evaluation system arranged at the central station, or, to say it in other words, that it is now possible, in addition to the transmission of the supply voltage to the respective measuring head, to implement bidirectional signal transmission between the measuring head and the central electronic evaluation system.

ADVANTAGES OF THE INVENTION

The invention solves this problem with the aid of the characterizing features of the main claim and provides the advantage that by dividing the "site equipment" into an intelligent measuring head, which may for example be equipped directly with a microprocessor, and means for receiving at least two sensors in addition to the temperature sensor normally used, bidirectional digital data communication, i.e. digital signal transmission between the electronic central station and the measuring head is rendered possible in both directions so that any susceptibility to trouble is almost fully eliminated in this area.

In addition, it is now possible to connect to a single 2-wire line basically any desired number of "site devices", each consisting of a measuring head comprising at least two gas sensors and a temperature sensor, with the possibility to select series and parallel connections as desired.

If under exceptional circumstances, i.e. under explosive conditions, the line current may not exceed certain given values and the number of measuring heads, including their sensors, has to be limited, the lines leading to the central electronic evaluation system may be linked within the latter by the usual means of information technology.

Another advantage of the invention is seen in the high measuring security, the required low maintenance input and the low-cost and simple installation, it being an additional particular advantage that the measuring heads may be equipped with any desired type of sensors, which means that when one or both or even more sensors of a measuring head have to be exchanged because of aging effects, or the like, the sensors newly installed in the standard or universal measuring head, in replacement for the old sensors, may either be identical to the latter or be designed for detecting different gases and/or for other measuring ranges. This is due to the fact that two different identification systems are incorporated into the gas detection system according to the invention, i.e. on the one hand an identification between the respective sensors connected to a measuring head, and on the other hand the possibility to address the sensors from the central electronic evaluation system as the central station, so that the existing two-wire line can be used without any problems for having the measuring data of plurality of "site devices" recorded by the central electronic evaluation system, with extremely short cycle times.

In addition to the options provided for the equipment of the respective measuring head, the invention provides the possibility to perform dynamic temperature corrections, to monitor automatically the service life of the sensor by means of a special service signal, to perform automatic measuring compensation and range balancing, due to the sensor identification feature, and does away for the same reason with any balancing requirements when replacing existing sensors by identical or different sensors (exchange of sensors). The two-wire connection cable used may be installation or telephone cables, the possible transmission distances being in the range of up to 5000 m. In the case of the particular embodiment described herein, which is however not intended to restrict the invention, transmission is effected bidirectionally for 3 measuring values (gas sensors and measured temperature value) and additional 8 status signals, at a transmission rate of 1200 baud, via a telephone cable serving as digital bus. The sensor identification is transmitted in this case by the "site electronics", for example a microprocessor arranged in the measuring head, and at the same time the service life of the sensor is monitored automatically.

Another particular advantage of the present invention is further seen in the fact that the "site electronics" now permit automatic system calibration by means of a special calibration cap, without the need for a manual balancing operation. As the corresponding values are stored in the central electronic evaluation system, for example in an EPROM, the central electronic evaluation system is informed, by the identification of the sensor connected to the respective addressed measuring head, of the charactristics of the sensor, i.e. the gases it is capable of detecting and its measuring ranges. The identification may, for example, be detected physically by the intelligent measuring head, through a binary code, when the sensor is inserted in or mounted on the measuring head, and may then be held available for enquiry by the central electronic evaluation system.

The features described by the subclaims permit advantageous improvements and developments of the gas detection system specified by the main claim. A particularly advantageous variant provides that the identification of each sensor takes the form of terminals arranged in the form of a binary code, for example by simply bridging soldered points according to the binary system, depending on the desired identification. This identification is given to the sensors already at the factory, before delivery, so that the sensors can be replaced later at desire as the intelligence of the measuring head will automatically inform the central electronic evaluation system of the type of sensor inserted, and it measuring range. It is then possible to provide a suitable display at the central station which automatically indicates the correct concentration and the component measured at any time. Compared with the known, lengthy measuring method using hose connections or multi-wire shielded cable lines for each measuring head, the invention therefore succeeds in achieving a really revolutionary simplification and measuring security over the prior art, as regards the detection of the presence of gases and their concentration.

BRIEF DESCRIPTION OF THE DRAWINGS

Certain embodiments of the invention will be described hereafter with reference to the drawing in which.

DESCRIPTION OF THE EMBODIMENTS

It is the basic idea of the present invention to provide local communication means, in the field of gas analysis, between the sensor/measuring head on the one hand and the central electronic evaluation system on the other hand, by giving the measuring head its own intelligence, for example in the form of a single-chip computer, a microprocessor, or the like, and by having the signals transmitted digitally in both directions, and by performing the data exchange between the different measuring heads and the central electronic evaluation system simultaneously and in serial succession, while the measuring heads are simultaneously supplied with the required supply voltage via a transmission line.

Figures 1, 4:
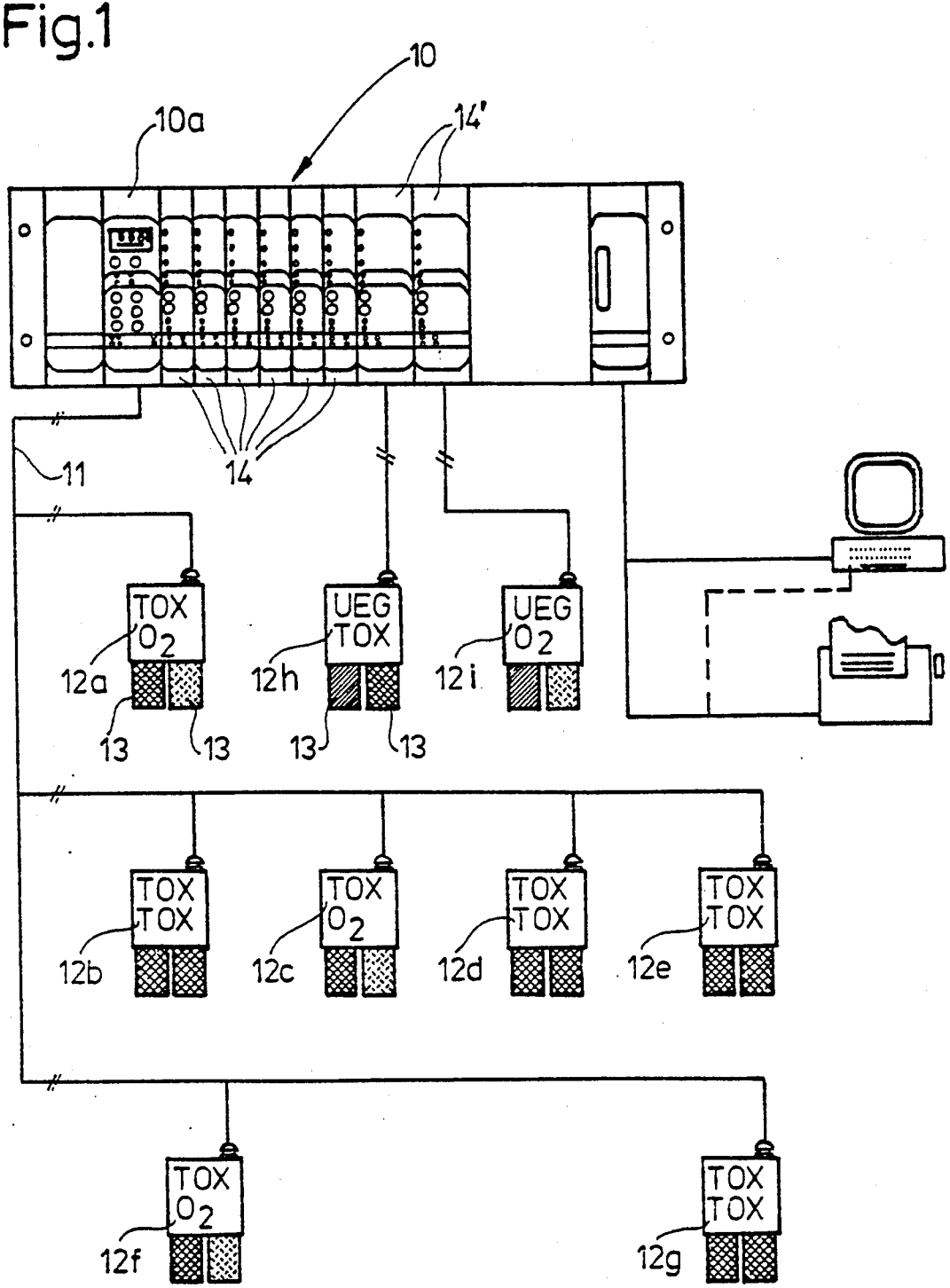
FIG. 1 is a diagrammatic representation of the different possibilities of connecting the individual measuring heads and the central electronic evaluation system.
FIG. 4 is an end perspective view of a sensor in accordance with the invention having an identification code in the connector pins.

In FIG. 1, one can see the central electronic evaluation system 10 and a common two-wire line 11 connecting the said system to the measuring heads 12a, 12b . . . 12g.

If very high currents are required by the measuring heads, as indicated in the drawing by 12j and 12k, it is also possible to provide a separate connection line whose digital signals are also supplied to the central electronic evaluation system 10, via suitable circuit means.

Each of the measuring heads 12a to 12i comprises a separate microprocessor and may be equipped with a plurality, in the illustrated embodiment with two, of sensors having the most different functions for gas analysis purposes. In the particular embodiment illustrated in the drawing the sensors are designed to detect only toxic, explosive, or oxygen mixtures, as indicated at the measuring heads, although it would of course be possible also in the illustrated case, where each head is equipped with two sensors, to implement any desired combination, for example one sensor for toxic and one sensor for explosive gas, or two sensors for toxic gas mixtures of different components, or a combination of one oxygen sensor with one sensor for toxic or explosive gas mixtures, and in addition it would also be possible to employ a plurality of sensors for detecting one and the same gas, but for different measuring ranges.

The abbreviations used in FIG. 1 for describing the functions of the individual sensors and/or measuring heads are TOX for the detection of toxic gases, UEG for the detection of explosive gases or gas mixtures, 02 for the detection of oxygen or lack of oxygen, to give only a few examples of the possibilities that are opened up by the invention.

All sensors illustrated in FIG. 1 are designated by reference numeral 13, regardless of their type or function (measuring range). The additional temperature sensors equipping advantageously each measuring head are not shown in the drawing for the sake of clarity.

In the central electronic evaluation system, a main computing unit comprising extensive storage capacities is designated by reference numeral 10a in the plug-in area. A two-wire line 11 connects this unit to the measuring heads 12a to 12g. The main computing unit contains data relating to each of the measuring heads 12a to 12g connected to it so that each of these measuring heads can be addressed by it by means of a predetermined code, in a desired predetermined order (there also exist different methods which permit certain priority measuring heads to be enquired by preference, which methods need not be described here in greater detail as they are known as such) which then gives rise to the bidirectional serial transmission of a protocol. Each measuring head forms an interface between the central electronic evaluation system and the sensors 13 connected to the latter. During the normal cyclical enquiry sequence (for the purposes of these explanations, the calibration steps are initially left out of regard) this interface is supplied by the respective measuring head with the sensor identification S1 or S2 for the connected gas sensors, and S3 for the temperature sensor, and then with corresponding, standardized measuring values in a binary coded form, after the latter have been processed by the intelligence of the measuring head, on the analog side, to derive voltage values between 0 and 1 V, and have then be digitized, and supplemented by adjustments for peripheral conditions, such as temperature compensation, corrections for particular characteristics, linearization and other corrections, for example for humidity or air pressure influences.

The measuring-head interface starts the process by addressing a corresponding storage area in the main computing circuit 10a of the central electronic evaluation system, using the supplied sensor identification, so that the measuring value transmitted by that sensor subsequently —or before—via the line in a coded binary, i.e. digital form can be classified and evaluated correctly.

In fact, there are still other plug-in units in the area of the central electronic evaluation system, all of which are designated generally by reference numeral 14, and which are assigned to the individual measuring heads or sensors, for receiving from the main computing circuit 10a the measured values recorded for the respective sensor so that the plug-in unit assigned to the respective sensor is then capable of displaying the measured values so recorded in a suitable form, together with the other possible displays, such as alarm, diagnosis, trouble, calibration, and operating conditions, which are usually indicated by luminous diodes or other lamps. Consequently, the central electronic evaluation system, together with its main computing circuit, may be regarded as the administrator of the data received and transmits the latter via an internal bus to the plug-in units 14 where they can be redistributed according to their respective measuring points, if and to the extent this should be necessary or desirable.

Given the numerous possibilities of this type of data collection and administration, there are of course many possibilities of taking into account other aspects, in addition to recording the environmental temperature dynamically at the measuring points, as for instance the remaining service life of the individual sensors, which can be derived without any problems from their general service life and the data stored in the main computing circuit. When a sensor is exhausted, it is then possible to have this information displayed on the corresponding plug-in unit.

In addition, the indicated temperature may warn the operator, who is of course constantly watching the central electronic evaluation system with its plug-in units in the central station, of the development of any dangerous conditions in its system, and the location thereof, for example of flames or fire, as such data are of course also transmitted by the temperature sensor.

It goes without saying that any functions that are not performed by the electronic system of the measuring head, especially by its microprocessor, because of its particular design or limitations, are then performed by the main computing circuit 10a as part of the processing of the data transmitted by the sensors, giving due regard to the data stored and any corrections that have to be made. This distribution of functions may be selected as desired, although it must be ensured that the main computing circuit 10a, with its storage capacities, must in any case be informed of the conditions which have given rise to the momentary measured value transmitted by the sensor.

In any case, the environmental temperature of the measuring head will be displayed in the central station so that there is always the possibility to have the temperature sensitivity of the sensors compensated in the area of the central electronic evaluation system.

In practice, two sensor housings are (initially) mounted on each measuring head (for gas analysis, it being of course also possible, depending on the design of the interface area, the storage capacitites and the set-up of the central electronic evaluation system, to connect additional sensors if this should prove necessary). For example—to give a few figures—10 sensors of different types with, for example, 30 different measuring ranges may be provided. In case of failure, or if the operator so chooses, the sensors of any measuring head may be exchanged without any problems, according to their type and the measuring area, if the measuring head has to be exchanged for one adapted to different gas components or other measuring ranges. The electronic system of the microprocessor arranged in the measuring head, together with the digital transmission of the signals in both directions, allow any such exchange of sensors without any problems, due to the special identification of the sensors.

Figure 2:
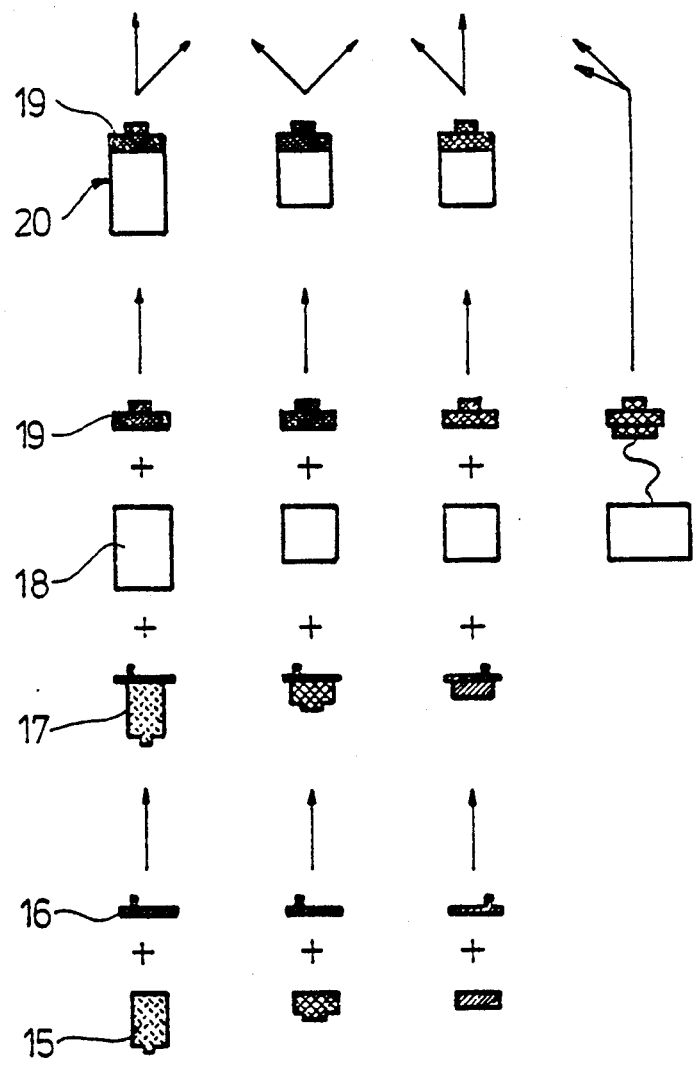
FIG. 2 illustrates, step by step, the structure of different sensor components and their assignment to the individual measuring heads.

FIG. 2 illustrates in this connection different sensor structures; the properties of the sensor are indicated below the latter by the corresponding abbreviations (02, TOX, UEG, IRA, the latter standing for infrared gas analysis).

The sensor element 15 as such is connected to a simple electronic system 16, and these two components together are arranged in a sensor housing 18 with the associated base 19, as sensor unit 17. One then obtains a typical sensor component 20, in any case one with uniform bases 19 which can be mounted on the measuring heads 12 shown on top of the drawing, by inserting the base 19 into suitable plug-in contacts, as indicated in the drawing, whereby the electric connections are simultaneously established. As has been mentioned before, it is important that the identification of each sensor be arranged at the base or base portion 19 of the sensor in a manner that can be read by the measuring head. The sensor-related identification is provided on the respective sensor already in the course of its production so that the sensor can be exchanged later at the site at desire; the measuring head in its capacity as interface will in any case record the identification and inform the central electronic evaluation system automatically of the type of sensor present, and its measuring range.

Advantageously, this coding relating to the type and measuring ranges is enquired and compared automatically during each enquiry cycle, in which case the corresponding processing routines for each sensor identification are stored in the storage (preferably a so-called EPROM) of the central electronic evaluation system so that the correct concentration and the component in question can be indicated automatically on corresponding, associated displays. It has been mentioned before that, according to a preferred embodiment of a sensor, the identification is realized by connecting electric contact points by means of bridges in the base area. This makes it possible for the microprocessor in the measuring head to pick up the necessary information, and for the same reason no balancing operation is required when a new sensor is mounted.

Another advantage is seen in the fact that this basic design of the current supply in the area of the measuring head and of the digital transmission of the measured values and status signals makes it possible, without any problems, in any case for sensors requiring only low supply currents, to use enclosure type EEx ib (for the sensors EEx di) lines for the wiring system proper. In cases where excessively high currents prohibit the use of a single two-wire line 11 (FIG. 1) measuring heads 12h and 12i may be provided and connected to the respective plug-in units 14' via separate lines.

In goes without saying that the system can be connected, via the internal bus line in the central electronic evaluation system 10 and corresponding interface circuits, to a higher-ranking computer capable of printing out and registering the measured values and status values, as well as other operating conditions, according to selected criteria.

The basic concept described heretofore permits an additional embodiment of the invention to be implemented, namely the fully automatic calibration of the gas sensors in the area of the central station. In this case all risks of operating faults and errors are absolutely excluded because it is then only necessary for a single operator to handle the sensor directly at the site.

Figure 3:
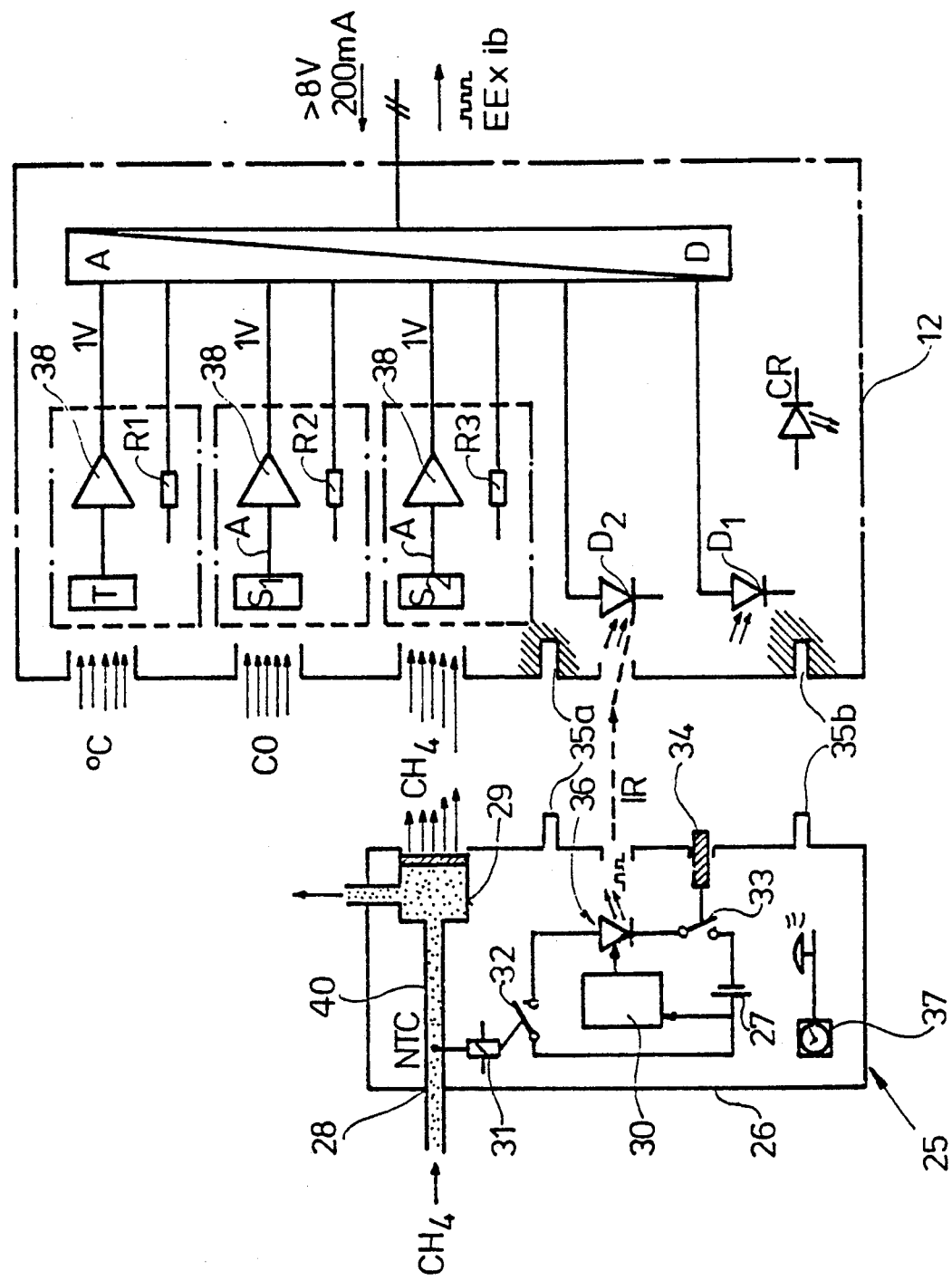
FIG. 3 is again a diagrammatic representation of a calibration system of the type now rendered possible in connection with the present invention.

FIG. 3 illustrates diagrammatically the basic principle underlying the calibration process.

A calibration device 25 taking in practice the form of a calibration cap, is placed over each of the sensor housings which remain firmly connected to the measuring head. The calibration cap 26 is provided with current supply means of its own, for example a battery 27, an external gas connection 28, a cap-shaped housing—indicated at 29—of a design and shape permitting it to be placed over the gas-sensitive area of the sensor component in sealed relationship, and an electronic area 30 generating the calibration signals which are to be picked up by the measuring head.

Gas sensors may require to be calibrated as to their zero point and sensitivity (steepness). For each calibration a test gas of a predetermined concentration has to be connected to the gas connection 28. The line 40 leading from the external gas connection 28 to the cap 29 is equipped with a flowmeter, preferably in the form of an NTC resistor, which determines the presence of the calibration gas flow and actuates a first switch 32, for example by means of an intermediate relay 31. When being fitted mechanically upon the sensor housing, the calibration cap may at the same time actuate a second switch 33, for example by means of a simple pin 34 which is pressed down by the mounting operation. It goes without saying that switching may also be effected by other means, for example manually by the operator after he has fitted the calibration cap. The calibration cap may further comprise guide means 35a, 35b serving to connect the sensors correctly to the measuring head, and it is of course also possible to have the calibration of both or more gas sensors at the measuring head and also at the temperature sensor carried out fully automatically. In FIG. 3, the two sensors used in this case are designated by S1 and S2, and the temperature sensor is designated by T.

If both switches 32 and 33 are in the closed condition, a suitable transmitter 36 provided in the area of the calibration cap 25, preferably a luminous diode supplied with a suitable coded binary signal or simply with a predetermined frequency (1 kHz), generates a signal, for example this 1 kHz signal (for example in the infrared range) and supplies the latter to a receiver diode D2 in the measuring head assigned to the sensor S2.

In the presence of the correct calibration gas flow, the calibration then generates the calibration signal (initially for a first sensor S2); the microprocessor of the measuring head 12 recognizes the calibration signal and transmits it to the central electronic evaluation system so that the latter commences a "calibration phase" in communication with this particular measuring head, while the central electronic evaluation system supplies an acknowledgement signal to the measuring head confirming that the signal has been recongized and that the system is ready for calibration. This acknowledgement signal is displayed in a suitable manner on the measuring head, by means of a luminous diode CR, which means that the "calibration" signal lights up to inform the operator that the total processor system is accepting and receiving the calibration values.

In this connection, the following should be noted: Given the fact that the central electronic evaluation system must be capable of recognizing whether the gas present is a so-called zero gas intended for determining the zero point, or a test gas intended for determining the sensitivity, the central electronic evaluation system will interpret any gas concentrations of, for example, less than 10% recorded during the "calibration phase" as calibration or zero gas for determining the zero point, and any concentrations above 20%, for example, as test gas for determining the sensitivity. The test gas may then have a predetermined concentration of, for example, 50% of the final value of the measuring range. As a result of the values and data stored in the central electronic evaluation system, the latter is informed of the composition of the gas with which it is confronted and is in a position to carry out the corresponding calibration processes automatically.

The calibration operation proceeds, on principle, as follows: As the measuring values are received during the calibration phase, the central electronic evaluation system monitors the incoming signal to detect the point where the concentration does no longer change, i.e. where the "concentration signal" assumes a zero state or any other stable state for a predetermined period of time. The central electronic evaluation system takes this condition as an indication that the sensor has assumed a balanced condition and is transmitting the test gas concentration, and corrects, if necessary, the zero point and steepness (sensitivity) data of this respective sensor stored in it, whereafter the calibration process is terminated, preferably not by the operator but automatically on instructions received from the central electronic evaluation system. Upon termination of the calibration process, the central electronic evaluation system removes the "calibration" signal (lamps of the diode CR), or causes the latter to light up intermittently so as to inform the operator that the calibration process for this particular sensor has been terminated and that the calibration cap can be removed and placed upon the next sensor of the same measuring head, for calibration thereof. The calibration cap 25 is then fitted on the other sensor, the calibration signal is again generated by the calibration cap and supplied to a second receiver in the form of a photodiode D1. The frequency generated may now be 2 kHz, for example. In this case, the—different—calibration signal may even be supplied to the same receiver in the measuring head, and it would also be possible to give the calibration cap immediately a design comprising two adjacent partial caps by which the sensors on the measuring head can be supplied with the test gases in succession.

In addition, the calibration cap may be provided with a circuit 37 generating its own timing pulse. It should be noted expressly in this connection that the calibration may be performed by adjusting corresponding circuits in the area of the measuring head and/or by storing the new data resulting from the calibration in the measuring head. This is advantageous also insofar as the measuring head is anyway provided with electronic means 38, which are indicated in FIG. 3 by the amplifier symbol only and which are associated with each sensor so as to permit it, in its capacity as interface, to output standardized measuring signals of between 0 and 1 V in a binary coded form.

In summary, it can be noted that the gas detection system, including the measuring head and the central electronic evaluation system, detects automatically that the calibration process is running; it monitors the calibration process automatically and takes over the calibration values automatically, keeping the operator constantly informed, so that all the problems encountered according to the prior art in connection with the calibration of gas sensors, which always has to be performed, have been eliminated all at once. The operator charged with carrying out the calibration only has to fit the calibration cap over the sensor housing and to supply the system with the correct test gas. All other operations are carried out automatically, due to the capability of the system to communicate in both directions so that any errors are absolutely excluded.

All features mentioned or shown in the above description, the following claims and the drawing may be essential to the invention either along or in any combination thereof.

I claim:

1. A gas detection system for detecting the content of gases, comprising:
   a plurality of measuring heads, each said head being positioned at a measuring point, each said measuring head being equipped for connection with a least one sensor, said sensors being one of the same and different types, sensors of the same type having one of the same and different measuring ranges;
   a central electronic evaluation system, said evaluation system being connected to said plurality of measuring heads by means of a common two-wire line, said common two-wire line between said central electronic evaluation system and said measuring heads being adapted for bidirectional digital communication and, simultaneously, for supplying electrical operating current to said measuring heads;

each said measuring head having its own processing means for at least partially processing the signals supplied by each said sensor attached thereto, each said sensor having an identification indicative at least of its type, measuring component and measuring range, said identification being detected by the processing means of the associated measuring head upon connection of said sensor to said associated measuring head, 2. A gas detection system as in claim 1, wherein said sensors have uniform base connections, and said measuring heads have corespondingly configured connections so that said sensors may be joined to said measuring heads, said sensor identifications being in a form of electrical contacts subject to recognition by said associated measuring head when said sensor and associated head are connected.

3. A gas detection system as in claim 1, wherein each said sensor is provided with soldered contact bridges that are subject to identification by the measuring head when said measuring head and said sensor are connected, said bridges indicating the type, gas component to be meansured and measuring range of the sensor in a binary coded form.

4. A gas detection system as in claim 1, and further comprising storage means holding data relating to the sensor type, gas component to be measured and the measuring range assigned to a specific sensor, said central electronic evaluation system evaluating signals received from respective sensors after said evaluation system receives sensor identification from said measuring head, said evaluation using said stored data.

5. A gas detection system as in claim 4, wherein processing routines for each sensor type are stored in said storage means of said central evaluation system.

6. A gas detection system as in claim 4, wherein said evaluation system includes an internal bus and said measured data recorded and processed by said central electronic evaluation system for each sensor, respectively, is distributed correspondingly and supplied via said internal bus to separate plug-in units including displays indicating different operating conditions and functions of each said measuring head.

7. A gas detection system as in claim 1, wherein said processing means at each said measuring head receives analog data from the associated sensors, converts said data to digital format, linearizes, corrects and compensates, when necessary, for humidity and air pressure effects, respectively, said digital data being supplied to said central electronic evaluation system together with sensor identification data.

8. A gas detection system as in claim 1, and further comprising a temperature sensor on a measuring head, instantaneous temperature values of the environment at the measuring point being measurable by said temperature sensor for transmission to said central electronic evaluation system.

9. A gas detection system as in claim 1, wherein for calibrating said sensors a calibration means is provided that automatically starts and performs the calibration process by its own signals when said calibration means is applied to a measuring head, said calibration signals being received by said measuring head and transmitted to said central electronic evaluating system.

10. A gas detection system as in claim 9, wherein said calibration means includes a calibration cap, said cap having a special outlet for supplying calibration gas to gas-sensitive elements of each sensor, said measuring head including a receiving unit, said calibration means applying the calibration signal to said receiving unit when said calibration cap is placed in its calibration position and a calibration gas is supplied to said gas-sensitive element.

11. A gas detection system as in claim 10, wherein said calibration cap provides to said measuring head and to said central electronic evaluation system a specific calibrated signal related to the respective sensor being calibrated.

12. A gas detection system as in claim 10, wherein said calibration signal from said calibration cap is a pulsed infrared signal of a predetermined frequency, said signal being generated by a transmitter diode and supplied to a receiver diode in said measuring head, a flow sensor in said calibration cap indicating the presence of a calibration gas and one of a contact sensor and switch indicates that said cap has been applied to the sensor to be calibrated.

13. A gas detection system as in claim 12, and further comprising said contact sensor, and wherein said flow sensor is an NTC resistor connected in series with said contact sensor, said contact sensor being adapted to activate said transmitter diode to emit said calibration signal.

14. A gas detection system as in claim 9, wherein said central electronic evaluation system, after receiving said calibration signal and identification of a respective sensor from the associated head, supplies a calibration acknowledgement signal to the associated measuring head, said measuring head supplying a signal acknowledging said calibration, said central electronic evaluation system storing the measured value from said sensor and indicating the end of the calibration process by inducing said calibration acknowledgement signal.

15. A gas detection system as in claim 14, wherein during a calibration, said signal electronic evaluation system monitors the measured value received from the associated sensor for a predetermined period of time for continuity of the sensors behavior over said time period, said associated sensor being supplied with calibration gas, said evaluation system storing and accepting new calibration values for a detected concentration of a first test gas at zero value and calibration values for a concentration of a second test gas exceeding such predetermined value as a sensitivity value of a predetermined magnitude.

16. A gas detection system as in claim 15, wherein during calibration, a measuring signal from a sensor remaining below a predetermined threshold is interpreted as belonging to said first test gas, a measuring signal exceeding a predetermined threshold being interpreted as representing a calibration gas of a known concentration.

17. A gas detection system as in claim 1, wherein during communication, said respective heads are addressed by said central evaluation system successively, in a predetermined sequence, and the measured value from each said sensor is taken together with its identification data.

18. A gas detection system as in claim 1, wherein, sensors are respectively capable of detecting inflammable, explosive and toxic gases and oxygen content or lack of oxygen.

19. A gas detection system as in claim 1, wherein there is one common two-wire line.

20. A gas detection system as in claim 1, and further comprising at least one additional two-wire line in parallel with said common two-wire line, said at least one additional wire line connecting to additional measuring heads for sensors.

* * * * *